(12) United States Patent
Hara et al.

(10) Patent No.: US 8,709,273 B2
(45) Date of Patent: Apr. 29, 2014

(54) SULFONATED AMORPHOUS CARBON, PROCESS FOR PRODUCING THE SAME AND USE THEREOF

(75) Inventors: Michikazu Hara, Yokohama (JP); Kazunari Domen, Yokohama (JP)

(73) Assignee: Tokyo Institute of Technology, Tokyo (JP)

( * ) Notice: Subject to any disclaimer, the term of this patent is extended or adjusted under 35 U.S.C. 154(b) by 958 days.

(21) Appl. No.: 10/572,057

(22) PCT Filed: Sep. 8, 2004

(86) PCT No.: PCT/JP2004/013035
§ 371 (c)(1),
(2), (4) Date: Jul. 23, 2007

(87) PCT Pub. No.: WO2005/029508
PCT Pub. Date: Mar. 31, 2005

(65) Prior Publication Data
US 2008/0227996 A1    Sep. 18, 2008

(30) Foreign Application Priority Data

Sep. 16, 2003 (JP) .................. 2003-322400
Mar. 23, 2004 (JP) .................. 2004-084527

(51) Int. Cl.
*H01G 9/02* (2006.01)
*H01B 1/00* (2006.01)
*H01B 1/12* (2006.01)
*H01B 1/04* (2006.01)
*H01M 6/04* (2006.01)
*H01M 6/18* (2006.01)
*H01M 10/0562* (2010.01)
*H01M 8/10* (2006.01)
*C07C 309/00* (2006.01)

(52) U.S. Cl.
USPC .......... 252/62.2; 252/500; 252/502; 429/188; 429/304; 429/491; 562/89

(58) Field of Classification Search
USPC ......... 252/500, 62.2, 502; 429/188, 304, 491; 562/89
See application file for complete search history.

(56) References Cited

U.S. PATENT DOCUMENTS

| 5,993,996 A * | 11/1999 | Firsich ....................... 429/231.8 |
| 6,495,290 B1 | 12/2002 | Hinokuma et al. |
| 2002/0061431 A1 * | 5/2002 | Koyama et al. ................ 429/33 |
| 2002/0187403 A1 | 12/2002 | Hinokuma et al. |

FOREIGN PATENT DOCUMENTS

| JP | 3-167712 A | 7/1991 |
| JP | 11-135109 A | 5/1999 |
| JP | 2002-75420 A | 3/2002 |
| WO | WO-01/06519 A1 | 1/2001 |
| WO | WO-03/100889 A1 | 12/2003 |

OTHER PUBLICATIONS

Michikazu Hara et al., "A Carbon Material as a Strong Protonic Acid," Angrew. Chem. Int. Ed. 2004, 43, pp. 2955-2958.
The Office Action (including English translation), dated Nov. 21, 2008, issued in corresponding Chinese Patent Application No. 200480026547.3.

* cited by examiner

*Primary Examiner* — Harold Pyon
*Assistant Examiner* — Tanisha Diggs
(74) *Attorney, Agent, or Firm* — Birch, Stewart, Koalsch & Birch, LLP (57) ABSTRACT

An amorphous carbon having sulfonate group introduced therein is provided which is characterized in that chemical shifts of a condensed aromatic carbon 6-membered ring and a condensed aromatic carbon 6-membered ring having sulfonate group bonded thereto are detected in a $^{13}C$ nuclear magnetic resonance spectrum and that at least a diffraction peak of carbon (002) face whose half-value width ($2\theta$) is in the range of 5 to 30° is detected in powder X-ray diffractometry, and which exhibits proton conductivity. This sulfonated amorphous carbon is very useful as a proton conductor material or solid acid catalyst because it excels in proton conductivity, acid catalytic activity, thermal stability and chemical stability and can be produced at low cost.

17 Claims, 4 Drawing Sheets

SULFONATED AMORPHOUS CARBON, PROCESS FOR PRODUCING THE SAME AND USE THEREOF

This application is an application filed under 35 U.S.C. 371 of PCT/JP2004/013035, filed Sep. 8, 2004, which claims priority from Japan Application 2004-084527, filed Mar. 23, 3004 and Japan Application 2003-322400, filed Sep. 16, 2003.

TECHNICAL FIELD

The present invention relates to an amorphous carbon having sulfonate group introduced therein (also referred to as "sulfonated amorphous carbon", hereinafter). The sulfonated amorphous carbon can be used as a proton conductor material, a solid acid catalyst or the like.

BACKGROUND ART

Polymer electrolyte fuel cells have a proton conductive membrane placed between a fuel electrode and an air electrode. Since they can be reduced in size and weight, they are expected to be used as on-board automotive fuel cells.

As a proton conductive membrane for a polymer electrolyte fuel cell, Nafion (a trade name by DuPont) has been used. However, Nafion can hardly act to operate a cell at higher temperatures since it is poor in thermal stability and chemical stability. In order to produce satisfactory output in a Nafion-incorporating fuel cell even at lower temperatures, it is needed to use a large amount (about 40 to 60% by weight based on the weight of an air electrode) of a platinum-supported catalyst in the air electrode, causing the increase in cost of the fuel cell. Further, Nafion in itself is also expensive. Development of new proton conductor materials as alternatives to Nafion has currently been pursued, but has not yet reached the practical stage (Non-patent reference No. 1, Patent reference Nos. 1 and 2).

On the other hand, solid acid catalysts had been actively studied, since they do not require any process for their separation and collection such as neutralization and removal of salts and can produce desired products in an energy-saving manner without production of unwanted side products (non-patent reference No. 2). Consequently, solid acid catalysts including zeolite, silica-alumina and water-containing niobium have had a great success in the field of chemical industry and offered great benefits to society. Nafion mentioned above is also a very strong solid acid having hydrophilic properties (i.e., an ultrastrong solid acid) and is already known to act as an ultrastrong acid having an acid strength higher than those of liquid acids. However, polymeric solid acid catalysts including Nafion have such disadvantages that they are sensitive to heat and that they are too expensive to use on an industrial scale. Therefore, it is difficult to design industrial processes for the production of solid acid catalysts which are advantageous compared to liquid acid catalysts from the viewpoint of performance and cost, and current chemical industry seems to predominantly depend on liquid acid catalysts. Under these circumstances, the advent of solid acid catalysts which outperform liquid acids in performance and cost has been demanded.

[Non-patent reference No. 1] HIGH TEMPERATURE MEMBRANES FOR SOLID POLYMER FUEL CELLS, ETSU F/02/00189/REP, Contractor Johnson Matthey Technology Centre, Prepared by Martin Hogarth Xavier Glipa, Crown Copyright, 2001, Pi-15, particularly page 4, TableI 1.

[Non-patent reference No. 2] Ishihara, K; Hasegawa, A; Yamamoto, H. Angew. Chem. Int. Ed. 2001, 40, 4077.

[Patent reference No. 1] Japanese Patent Application Laid-open No. 2003-217341.

[Patent reference No. 2] Japanese Patent Application Laid-open No. 2003-342241]

DISCLOSURE OF THE INVENTION

Problems to be Solved by the Invention

As mentioned above, social demand for substances which can be used as proton conductor materials and solid acid catalysts has been largely grown. The present invention is made under these situations. Accordingly, the object of the present invention is to provide a novel substance which can be used as a proton conductor material or a solid acid catalyst.

Means for Solving the Problems

In order to solve the problems as mentioned above, the present inventors have made intensive and extensive studies. As a result, the inventors have found that an amorphous carbon produced by heat treatment of an aromatic hydrocarbon in concentrated sulfuric acid or fuming sulfuric acid has proton conductivity and acid catalytic activity and also has high thermal stability and chemical stability. Based on this finding, the present invention has been accomplished.

That is, the present invention provides the following items (1) to (15).

(1) A proton conductor material comprising an amorphous carbon having sulfonate group introduced therein.

(2) The proton conductor material according to item (1), wherein the amorphous carbon having sulfonate group introduced therein has a proton conductivity of 0.01 to 0.2 $Scm^{-1}$ as measured by alternating current impedance method under the conditions of a temperature of 80° C. and a humidity of 100%.

(3) The proton conductor material according to item (1) or (2), wherein the amorphous carbon having sulfonate group introduced therein has a sulfur content of 0.3 to 15 atm %.

(4) The proton conductor material according to any one of items (1) to (3), wherein the amorphous carbon having sulfonate group introduced therein is produced by heat treatment of an aromatic hydrocarbon in concentrated sulfuric acid or fuming sulfuric acid.

(5) The proton conductor material according to item (4), wherein the heat treatment is performed at a temperature of 100° C. to 350° C.

(6) The proton conductor material according to item (4) or (5), wherein the aromatic hydrocarbon is at least one substance selected from the group consisting of benzene, naphthalene, anthracene, peryrene and coronene.

(7) An amorphous carbon having sulfonate group introduced therein characterized in that chemical shifts of a condensed aromatic carbon 6-membered ring and a condensed aromatic carbon 6-membered ring having sulfonate group bonded thereto are detected in a $^{13}C$ nuclear magnetic resonance spectrum and that at least a diffraction peak of carbon (002) face whose half-value width (2θ) is in the range of 5 to 30 is detected in powder X-ray diffractometry, the amorphous carbon having sulfonate group introduced therein exhibiting proton conductivity.

(8) The amorphous carbon having sulfonate group introduced therein according to item (7), wherein only a diffraction peak of carbon (002) face is detected in powder X-ray diffractometry.

(9) The amorphous carbon having sulfonate group introduced therein according to item (7) or (8), the amorphous carbon having sulfonate group introduced therein has a sulfonate density of 0.5 to 8 mmol/g.

(10) The amorphous carbon having sulfonate group introduced therein according to item (7) or (8), the amorphous carbon having sulfonate group introduced therein has a sulfonate density of 1.6 to 8 mmol/g.

(11) The amorphous carbon having sulfonate group introduced therein according to item (7) or (8), the amorphous carbon having sulfonate group introduced therein has a sulfonate density of 3 to 8 mmol/g.

(12) The amorphous carbon having sulfonate group introduced therein according to any one of items (7) to (11), wherein the amorphous carbon having sulfonate group introduced therein has a proton conductivity of 0.01 to 0.2 $Scm^{-1}$ as measured by alternating current impedance method under the conditions of a temperature of 80° C. and a humidity of 100%.

(13) A process for producing an amorphous carbon having sulfonate group introduced therein as recited in any one of items (7) to (12), comprising a step of performing heat treatment of an organic compound in concentrated sulfuric acid or fuming sulfuric acid.

(14) The process for producing an amorphous carbon having sulfonate group introduced therein according to item (13), wherein the step of performing heat treatment of an organic compound in concentrated sulfuric acid or fuming sulfuric acid is conducted in a stream of an inert gas or dry air.

(15) The process for producing an amorphous carbon having sulfonate group introduced therein according to item (13) or (14), further comprising, after the step of performing heat treatment of an organic compound in concentrated sulfuric acid or fuming sulfuric acid, a step of heating the heat-treated product under vacuum evacuation.

Effect of the Invention

The sulfonated amorphous carbon provided by the present invention is very useful as a proton conductor material or solid acid catalyst, because it is excellent in proton conductivity, acid catalytic activity, thermal stability and chemical stability and can be produced at low cost.

BEST MODE FOR CARRYING OUT THE INVENTION

Hereinbelow, the present invention will be described in detail.

[1] Sulfonated Amorphous Carbon

The sulfonated amorphous carbon according to the present invention is characterized in that it has the following properties (A), (B) and (C).

(A) In a $^{13}C$ nuclear magnetic resonance spectrum, chemical shifts of a condensed aromatic carbon 6-membered ring and a condensed aromatic carbon 6-membered ring having sulfonate group bonded thereto are detected.

(B) In powder X-ray diffractometry, at least a diffraction peak of carbon (002) face whose half-value width (2θ) is in the range of 5 to 30° is detected.

(C) It exhibits proton conductivity.

With respect to the property (B) above, a diffraction peak of a carbon face other than carbon (002) face may be additionally detected, but preferably only a diffraction peak of carbon (002) face is detected.

With respect to the property (C) above, the proton conductivity is not particularly limited, but is preferably 0.01 to 0.2 $Scm^{-1}$, more preferably 0.08 to 0.11 $Scm^{-1}$, wherein the proton conductivity is a measurement given by alternating current impedance method under the conditions of a temperature of 80° C. and a humidity of 100%.

Alternatively, the sulfonated amorphous carbon according to the present invention may have the following property (D) and/or (E).

(D) It has a sulfonate density of 0.5 to 8 mmol/g.

(E) It contains, based on the total number of carbon atoms, 3 to 20% of carbon atoms having a sulfonate group bonded thereto in its molecule.

With respect to the property (D) above, the sulfonate density may be 0.5 to 8 mmol/g, but is preferably 1.6 to 8 mmol/g, more preferably 3 to 8 mmol/g.

The sulfonated amorphous carbon according to the present invention can be used as a proton conductor material as described below, as well as a solid acid catalyst, an ion exchanger and an ion selective material.

[2] Production Process for Sulfonated Amorphous Carbon

Figure 1:
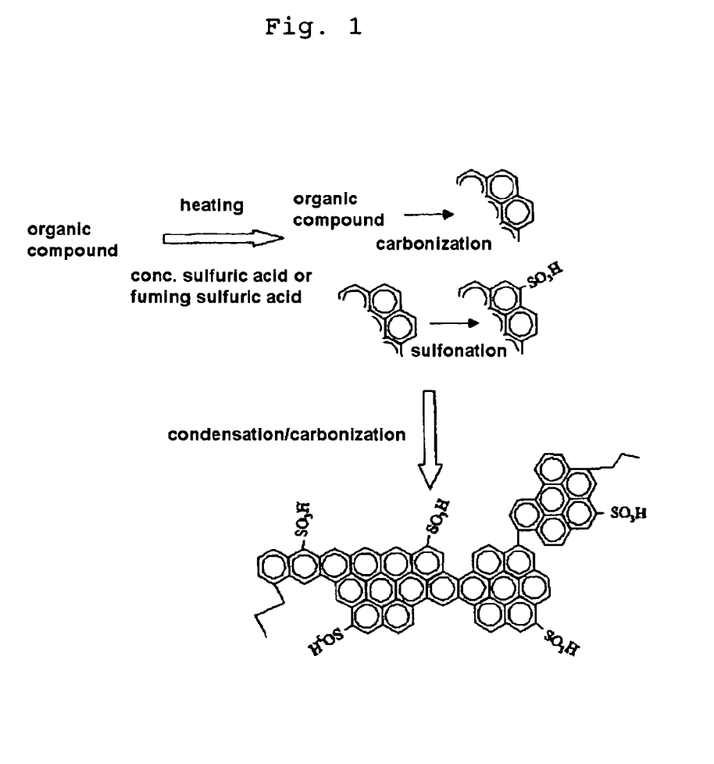
FIG. 1 is a schematic illustration showing the process for production of a sulfonated amorphous carbon from an organic compound.

The process for production of the sulfonated amorphous carbon according to the present invention involves a step of performing heat treatment of an organic compound in concentrated sulfuric acid or fuming sulfuric acid. This step is schematically illustrated in FIG. 1. An organic compound is treated with heating in concentrated sulfuric acid or fuming sulfuric acid to cause the carbonization, sulfonation and condensation of rings. As a result, an amorphous carbon having sulfonate group introduced therein as shown in FIG. 1 can be produced.

The heat treatment of the organic compound in concentrated sulfuric acid or fuming sulfuric acid is required to be performed in a stream of an inert gas (e.g., nitrogen, argon) or dry air in order to produce an amorphous carbon having a high sulfonate density. More preferably, the treatment is performed by heating concentrated sulfuric acid or fuming sulfuric acid containing the organic compound while blowing an inert gas (e.g., nitrogen, argon) or dry air thereinto. The reaction of an aromatic compound with concentrated sulfuric acid yields an aromatic sulfonic acid and water. Since this reaction is an equilibrium reaction, if the amount of water in the reaction system increases, then the reaction proceeds in a reverse direction rapidly, resulting in the remarkable decrease in the number of sulfonate groups which are introduced into the amorphous carbon. Accordingly, an amorphous carbon having a high sulfonate density can be synthesized by performing the reaction in a stream of an inert gas or dry air or by performing the reaction while blowing such a gas into the reaction system and removing water steadily from the reaction system.

In the heat treatment, sulfonation of the organic compound is allowed to cause in tandem with the progress of partial carbonization, cyclization, condensation of the organic compound and the like. The temperature for the heat treatment is not particularly limited as long as the reaction can proceed. However, from an industrial viewpoint, the temperature is usually within the range of 100 to 350° C., preferably 150 to 250° C. If the treatment temperature is below 100° C., then the condensation and carbonization of the organic compound may not be good enough and the carbon may be formed at an unsatisfactory level. If the treatment temperature exceeds 350° C., on the other hand, then the thermal decomposition of sulfonate group may occur.

The time period for the heat treatment may be suitably selected depending on the type of the organic compound used, the treatment temperature employed and the like, but is usually 5 to 50 hours, preferably 10 to 20 hours.

The amount of concentrated sulfuric acid or fuming sulfuric acid used is not particularly limited. However, the amount is generally 2.6 to 50.0 moles, preferably 6.0 to 36.0 moles, per mole of the organic compound.

As for the organic compound, an aromatic hydrocarbon may be used. Other organic compound such as a naturally occurring substance (e.g., glucose, sugar (sucrose), cellulose) and a synthetic polymeric compound (e.g., polyethylene, polyacrylamide) may also be used. The aromatic hydrocarbon may be a polycyclic or monocyclic aromatic hydrocarbon. For example, benzene, naphthalene, anthracene, perylene and coronene may be used, and naphthalene is preferably used. The organic compound may be used alone, or two more types of organic compounds may be used in combination. The organic compound used is not necessarily of purified form. For example, heavy oil, pitch, tar and asphalt containing an aromatic hydrocarbon may also be used.

When a naturally occurring substance such as glucose and cellulose or a synthetic polymeric compound is used as the starting material, the substance is preferably heated in a stream of an inert gas to cause the partial carbonization thereof prior to the heat treatment in concentrated sulfuric acid or fuming sulfuric acid. In this case, the heating temperature is generally 100 to 350° C. and the time period for the treatment is generally 1 to 20 hours. Preferably, the partial carbonization is allowed to proceed until a diffraction peak of carbon (002) face whose half-value width (2θ) is 30° is detected in powder X-ray diffractometry.

When an aromatic hydrocarbon or heavy oil, tar or asphalt containing the aromatic hydrocarbon is used as the starting material, after the heat treatment in concentrated sulfuric acid or fuming sulfuric acid, the heat-treated product is preferably heated under vacuum evacuation. This step enables to remove excess sulfuric acid, promote the carbonization and solidification of the product and increase the yield of the product. The vacuum evacuation is preferably performed using an evacuation system having an evacuation rate of 10 L/min or higher and an ultimate pressure of 100 torr or lower. The heating temperature is preferably 140 to 300° C., more preferably 200 to 280° C. The time period for the vacuum evacuation at these temperatures is generally 2 to 20 hours.

[3] Proton Conductor Material

The proton conductor material according to the present invention comprises an amorphous carbon having sulfonate group introduced therein. The proton conductor material of the present invention may be composed of only a sulfonated amorphous carbon or may additionally contain a component other than the sulfonated amorphous carbon.

The sulfonated amorphous carbon contained in the proton conductor material of the present invention may be any one as long as it has sulfonate group therein and can exhibit properties of an amorphous carbon. As used herein, the term "amorphous carbon" means a substance which is composed solely of the element carbon and does not have such a well-defined crystal structure as found in diamond and graphite. More specifically, the term means a substance in which any clear peak is not detected or a broad peak is detected in powder X-ray diffractometry.

Suitable examples of the sulfonated amorphous carbon include the sulfonated amorphous carbon of the present invention as described above and a sulfonated amorphous carbon having the property (C) described above as well as the following properties (F), (G) and (H).

(F) It is water-insoluble.

(G) It has an activity as an acid catalyst.

(H) It generally has a sulfur content of 0.3 to 15 atm %, preferably 3 to 10 atm %.

The proton conductor material according to the present invention is excellent in thermal resistance, chemical stability and cost-effectiveness and therefore is useful for use as a material for a proton conductive membrane for a fuel cell.

EXAMPLES

Hereinafter, the present invention will be described in great detail with reference to the following examples.

First, the apparatuses and methods for the measurements used in the examples are described.

Measurement of $^{13}C$ MAS (Magic angle spinning) nuclear magnetic resonance spectra: Measurement was made using ASX200 (Bruker, measurement frequency: 50.3 MHz).

X-Ray analyzer: Geigerflex RAD-B, CuKα (Rigaku Corporation, Japan) was used.

Elemental analyzer utilizing flash combustion: CHSN-932 (LECO, USA) was used.

Measurement of proton conductivity: Measurement was made in accordance with alternating current impedance method as follows. A film-like sample having a diameter of 10 mm which was placed under 100% of relative humidity was sandwiched between platinum electrodes and then packed in a sealed cell. The absolute value of impedance and the phase angle of the cell was measured using an impedance analyzer (HYP4192A) at a frequency of 5 to 13 MHz, an application voltage of 12 mV and temperatures of 20° C., 50° C. and 100° C. Based on the resulting data, complex impedance determination was made at an oscillation level of 12 mV by computation to calculate a proton conductivity.

Determination of sulfonate density: One gram of a material produced was dispersed in 100 mL of distilled water and then titrated with a 0.1 M aqueous sodium hydroxide solution to determine the sulfonate density. The point of neutralization was determined with a pH meter.

Example 1

Production of Sulfonated Amorphous Carbon from Naphthalene

Twenty grams of naphthalene was added to 300 ml of concentrated sulfuric acid (96%). The mixture was heated at 250° C. for 15 hours and then evaporated under reduced pressure at 250° C. to remove excess concentrated sulfuric acid, thereby yielding a black powder. The black powder was washed with 300 ml of distilled water, and this procedure was repeated until the amount of sulfuric acid remaining in distilled water after washing became negligible to detect by the elemental analysis to yield an amorphous carbon having sulfonate group introduced therein.

The sulfonated amorphous carbon powder was shaped under pressure to prepare a disk having a thickness of 0.7 mm and a diameter of 10 mm. Platinum was deposited on one side of the disk and the proton conductivity was then determined in accordance with the alternating current impedance method described above. It was confirmed that the proton conductivity of the amorphous carbon having sulfonate residue introduced therein measured at a temperature of 80° C. and a humidity of 100% was $1.1 \times 10^{-1}$ Scm$^{-1}$. This result demonstrates that the amorphous carbon having sulfonate residue introduced therein has a proton conductivity comparable to that of Nafion.

Example 2

Production of Sulfonated Amorphous Carbon from Coronene

Five grams of coronene ($C_{24}H_{12}$) was added to 100 ml of concentrated sulfuric acid (96%). The mixture was heated at 250° C. for 15 hours and then evaporated under reduced pressure at 280° C. to remove excess concentrated sulfuric acid, thereby yielding a black powder. The black powder was washed with 300 ml of distilled water, and this procedure was repeated until the amount of sulfuric acid remaining in distilled water after washing became negligible to detect by the elemental analysis to yield an amorphous carbon having sulfonate group introduced therein.

The powdery amorphous carbon having sulfonate residue introduced therein was shaped under pressure to prepare a disk having a thickness of 0.7 mm and a diameter of 10 mm. Platinum was deposited on one side of the disk and the proton conductivity was then determined in accordance with the alternating current impedance method described above. It was confirmed that the proton conductivity of the amorphous carbon having sulfonate residue introduced therein measured at a temperature of 80° C. and a humidity of 100% was $0.7 \times 10^{-2}$ Scm$^{-1}$. This result demonstrates that the amorphous carbon having sulfonate residue introduced therein has a proton conductivity comparable to that of Nafion.

Example 3

Production of Sulfonated Amorphous Carbon from Heavy Oil

Ten grams of heavy oil was added to 300 ml of concentrated sulfuric acid (96%). The mixture was heated at 250° C. for 15 hours and then evaporated under reduced pressure at 250° C. to remove excess concentrated sulfuric acid, thereby yielding a black powder. The black powder was washed with 300 ml of distilled water, and this procedure was repeated until the amount of sulfuric acid remaining in distilled water after washing became negligible to detect by the elemental analysis to yield an amorphous carbon having sulfonate group introduced therein.

The powdery amorphous carbon having sulfonate residue introduced therein was shaped under pressure to prepare a disk having a thickness of 0.7 mm and a diameter of 10 mm. Platinum was deposited on one side of the disk and the proton conductivity was then determined in accordance with the alternating current impedance method described above. It was confirmed that the proton conductivity of the amorphous carbon having sulfonate residue introduced therein measured at a temperature of 80° C. and a humidity of 100% was $1.0 \times 10^{-1}$ Scm$^{-1}$. This result demonstrates that the amorphous carbon having sulfonate residue introduced therein has a proton conductivity comparable to that of Nafion.

Test Example 1

X-Ray Structural Analysis

The structures of the amorphous carbons having sulfonate residue introduced therein produced in Examples 1 to 3 was analyzed using the X-ray analyzer described above. According to the results, no structure was confirmed from the X-ray diffraction patterns in any one of the amorphous carbons having sulfonate residue introduced therein produced in Examples 1 to 3. It is demonstrated that these substances are amorphous.

Test Example 2

Determination of Sulfur Content

Each of the amorphous carbons having sulfonate residue introduced therein produced in Examples 1 to 3 were burned in a stream of oxygen to determine the sulfur content using the elemental analyzer described above. As a result, it was confirmed that the amorphous carbons having sulfonate residue introduced therein of Examples 1, 2 and 3 had sulfur contents of 7.1 atm %, 1.5 atm % and 3.5 atm %, respectively, and that all of these substances had many sulfonate groups in their molecules.

Test Example 3

Evaluation of Thermal Stability

The amorphous carbons having sulfonate residue introduced therein produced in Examples 1 to 3 were determined on their decomposition temperatures by temperature-programmed desorption method (Bel Japan, Inc., Japan; Multitask TPD) and thermogravimetric analysis method (Shimadzu Corporation, Japan; DTG-60/60H). As a result, it was confirmed that the amorphous carbons having sulfonate residue introduced therein of Examples 1, 2 and 3 had decomposition temperatures of 250° C., 210° C. and 250° C., respectively, and that all of these substances had high thermal stability.

Test Example 4

Evaluation of Chemical Stability

Each of the amorphous carbons having sulfonate residue introduced therein produced in Examples 1 to 3 was evacuated under vacuum at 150° C. for 1 hour. To a mixed solution of 0.1 mol of acetic acid and 1.0 mol of ethyl alcohol was added 0.2 g of the product as a catalyst under an argon atmosphere. The resulting solution was stirred at 70° C. for 6 hours. The amount of ethyl acetate produced during this catalytic reaction was determined by gas chromatography. After the reaction was completed, each of the amorphous carbons having sulfonate residue introduced therein was collected, washed and used as a catalyst again in the same reaction. The amount of ethyl acetate produced in the reaction was also determined in the same manner. For comparison purposes, the amount of ethyl acetate produced was also determined using the same amount of Nafion as a catalyst.

Figure 2:
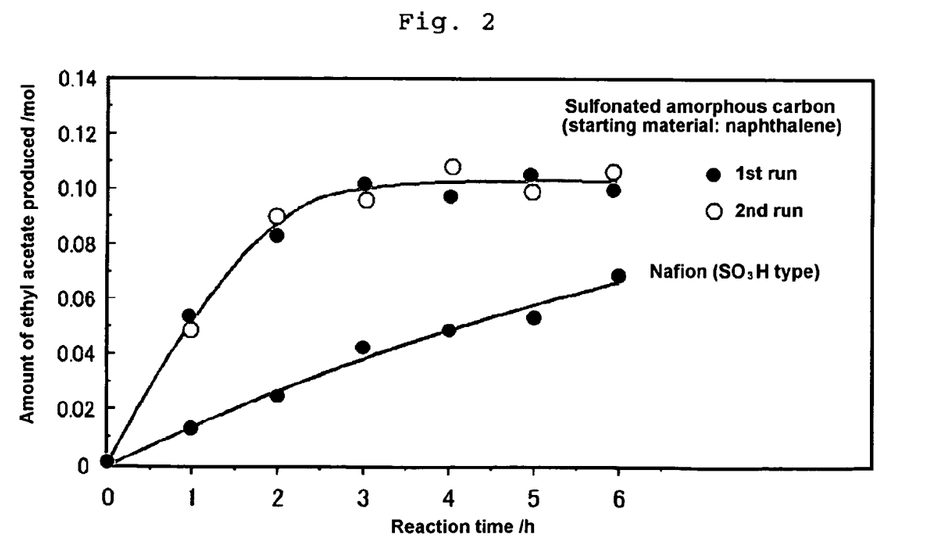
FIG. 2 is a graphical illustration showing the time course of the ethyl acetate production using a sulfonated amorphous carbon (starting material: naphthalene) as a catalyst.
Figure 3:
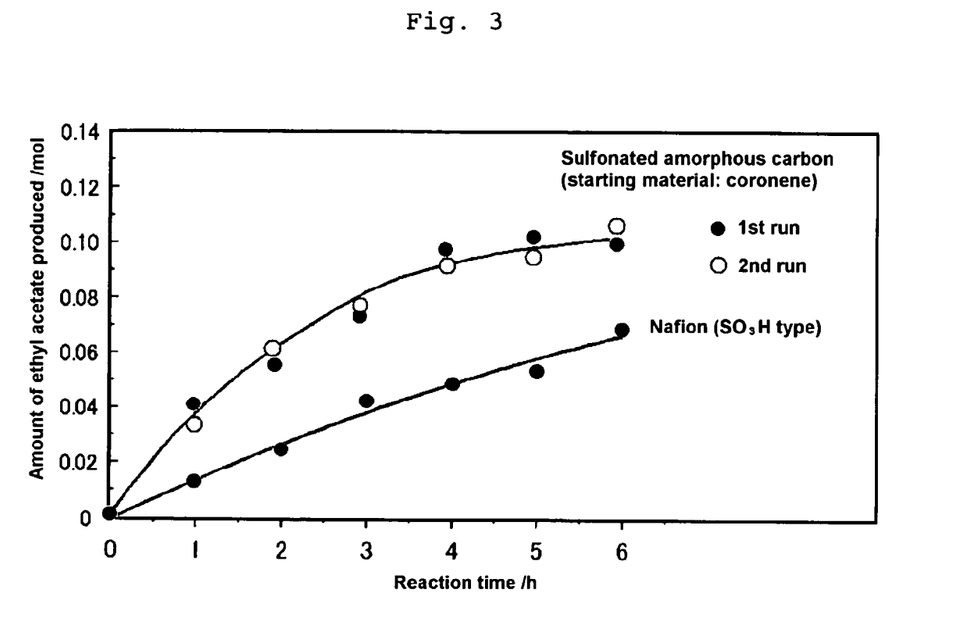
FIG. 3 is a graphical illustration showing the time course of the ethyl acetate production using a sulfonated amorphous carbon (starting material: coronene) as a catalyst.
Figure 4:
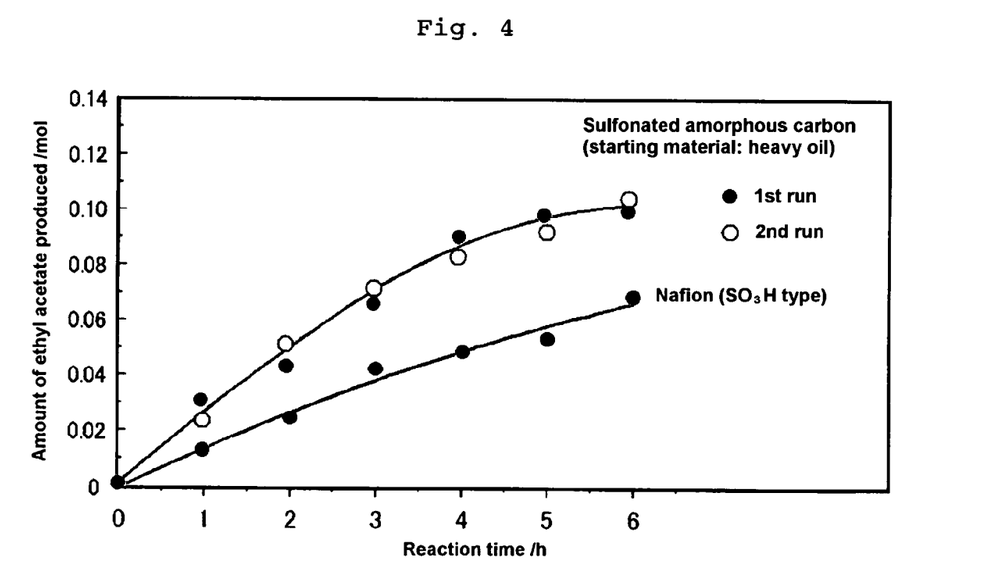
FIG. 4 is a graphical illustration showing the time course of the ethyl acetate production using a sulfonated amorphous carbon (starting material: heavy oil) as a catalyst.

The experimental results for the amorphous carbons having sulfonate residue introduced therein produced in Examples 1, 2 and 3 are shown in FIGS. 2, 3 and 4, respectively. As shown in the figures, all of the amorphous carbons having sulfonate residue introduced therein functioned as acid catalysts and their catalytic activities were higher than that of Nafion. The catalytic activities of the amorphous carbons having sulfonate residue introduced therein were not decreased even in their reuse.

Each of the amorphous carbons having sulfonate residue introduced therein was heated together with distilled water for 72 hours in an autoclave of 150° C. A powder was collected by filtration and evacuated under vacuum at 150° C. for 1 hour. Using 0.2 g of the product as a catalyst, the same reaction as described above was performed. All of these heat-treated amorphous carbons having sulfonate residue introduced therein exhibited the same catalytic activities as those of the heat-untreated counterparts (not shown). These results demonstrate that the amorphous carbons having sulfonate residue introduced therein have high chemical stability and that the acid strength of these substances is not deteriorated even in hot water of 150° C.

Example 4

(1) Production of Sulfonated Amorphous Carbon from Naphthalene

Figure 5:
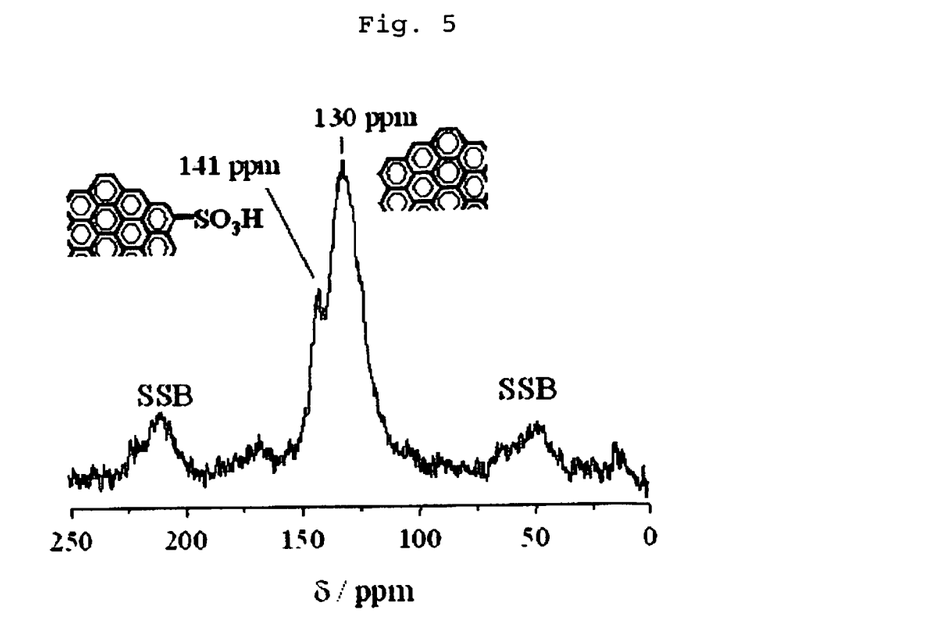
FIG. 5 is a $^{13}C$ nuclear magnetic resonance spectrum of a sulfonated amorphous carbon produced in Example 4.
Figure 6:
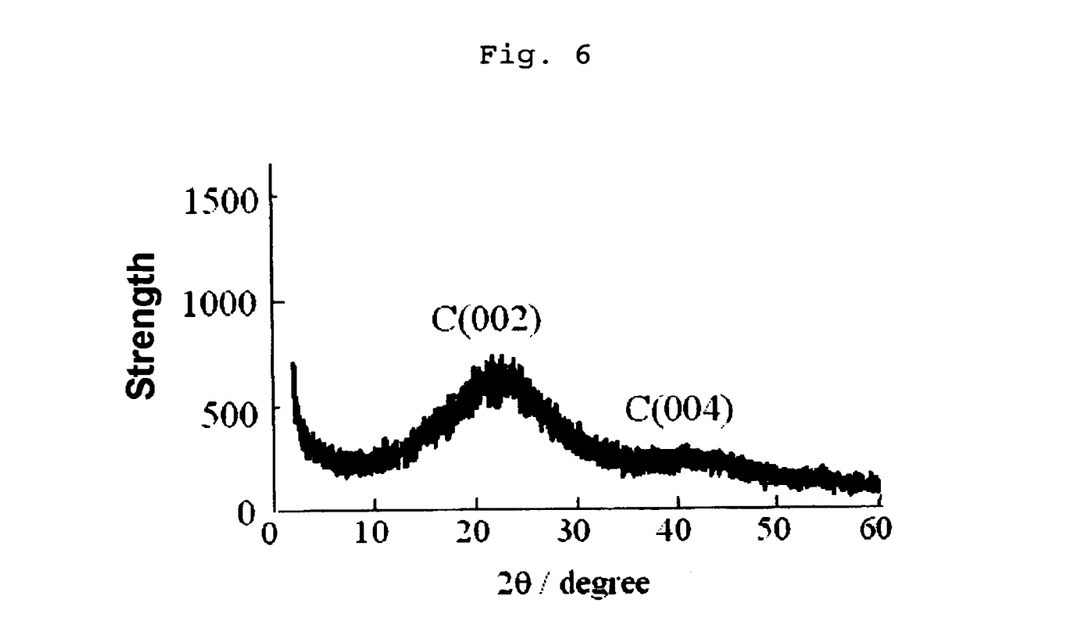
FIG. 6 is a powder X-ray diffraction pattern of a sulfonated amorphous carbon produced in Example 4.

Twenty grams of naphthalene was added to 300 mL of 96% concentrated sulfuric acid. The mixture was heated at 250° C. for 15 hours while blowing nitrogen gas into the mixture at a rate of 30 ml/min to yield a black liquid. The liquid was heated at 250° C. for 5 hours while evacuating under vacuum using a high vacuum rotary pump having an evacuation rate of 50 L/min and an ultimate pressure of $1 \times 10^{-2}$ torr or lower to remove excess concentrated sulfuric acid and promote the carbonization, thereby yielding a black powder. The black powder was heated at 180° C. for 12 hours in a stream of an inert gas and then washed with 300 mL of distilled water. This procedure was repeated until the amount of sulfuric acid remaining in distilled water after washing became negligible to detect by the elemental analysis on an elemental analyzer utilizing flash combustion described above to yield an amorphous carbon having sulfonate group introduced therein. The $^{13}C$ nuclear magnetic resonance spectrum of the sulfonated amorphous carbon is shown in FIG. 5. The nuclear magnetic resonance spectrum was measured in accordance with the $^{13}C$ MAS nuclear magnetic resonance spectrometry described above. As shown in FIG. 5, a chemical shift of a condensed aromatic carbon 6-membered ring was observed near 130 ppm and a chemical shift of a condensed aromatic carbon 6-membered ring having a sulfonate group bonded thereto was observed near 140 ppm. In FIG. 5, a peak indicated as "SSB" is not a band originated from carbon species, but a spinning side band which is typically observed in $^{13}C$ MAS nuclear magnetic resonance spectrometry. FIG. 6 shows a powder X-ray diffraction pattern of the sulfonated amorphous carbon measured using the X-ray analyzer described above. As shown in FIG. 6, diffraction peaks of carbon (002) face and carbon (004) face were confirmed. The half-value width (2θ) of carbon (002) face was 11°. The sulfonate density of the sulfonated amorphous carbon was 4.9 mmol/g.

The sulfonated amorphous carbon powder was shaped under pressure (JASCO corporation, Japan; a 10 mm-Φ tablet processor, processing conditions: 400 kg/cm², room temperature, 1 min) to prepare a disk having a thickness of 0.7 mm and a diameter of 10 mm. Platinum was deposited on one side of the disk and the proton conductivity was then determined in accordance with the alternating current impedance method described above. It was confirmed that the proton conductivity of the sulfonated amorphous carbon was $1.1 \times 10^{-1}$ Scm$^{-1}$. This result demonstrates that the sulfonated amorphous carbon has a proton conductivity comparable to that of Nafion.

(2) Use of Sulfonated Amorphous Carbon Produced from Naphthalene as Solid Acid

Figure 7:
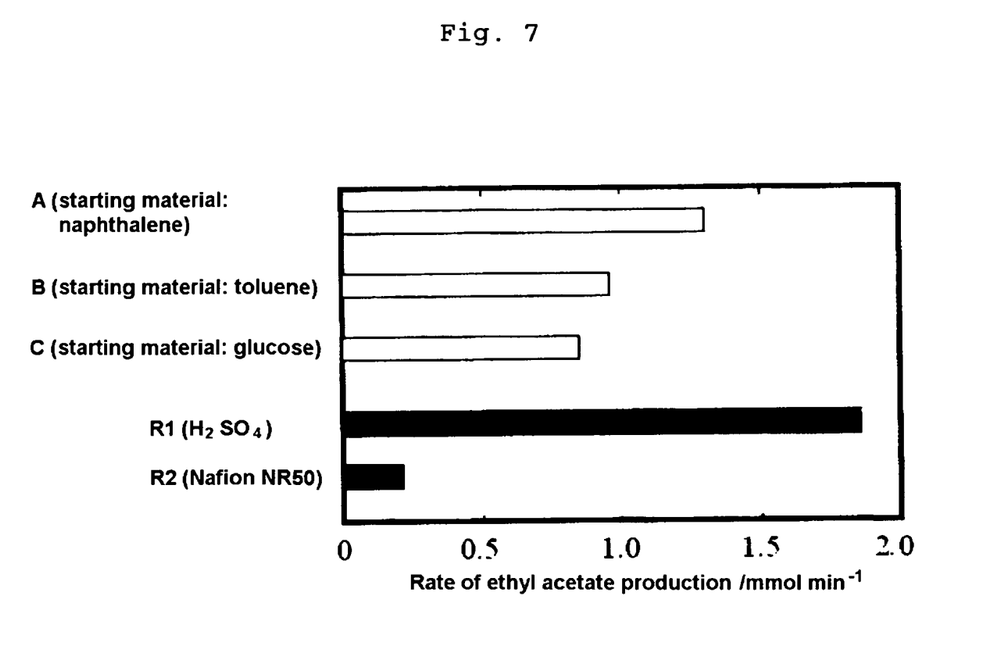
FIG. 7 is a graphical illustration showing the rate of ethyl acetate production of sulfonated amorphous carbons produced in Examples 4 to 6.

The sulfonated amorphous carbon powder was evacuated under vacuum at 150° C. for 1 hour. To a mixed solution of 0.1 mol of acetic acid and 1.0 mol of ethyl alcohol was added 0.2 g of the product as a catalyst under an argon atmosphere. The resulting solution was stirred at 70° C. for 6 hours. The rate of production of ethyl acetate during this catalytic reaction was determined by gas chromatography. The result was shown as "A (starting material: naphthalene)" in FIG. 7. For comparison purposes, the same reaction was performed using, in place of the sulfonated amorphous carbon, 0.2 g of each of concentrated sulfuric acid and Nafion as a catalyst to determine the rate of production of ethyl acetate. The results are also shown as "R1 ($H_2SO_4$)" and "R2 (Nafion NR50)", respectively, in FIG. 7. As shown in FIG. 7 as "A", the production of ethyl acetate was remarkably rapid in the presence of the sulfonated amorphous carbon, demonstrating that this substance functioned as a strong solid acid catalyst.

Example 5

(1) Production of Sulfonated Amorphous Carbon from Toluene

Five grams of toluene was added to 100 mL of 96% sulfuric acid. The mixture was heated at 250° C. for 15 hours while blowing nitrogen gas into the mixture at a rate of 30 ml/min to yield a black liquid. The liquid was heated at 250° C. for 5 hours while evacuating under vacuum using a high vacuum rotary pump having an evacuation rate of 50 L/min and an ultimate pressure of $1 \times 10^{-2}$ torr or lower to remove excess concentrated sulfuric acid and promote the carbonization, thereby yielding a black powder. The black powder was heated at 180° C. for 12 hours in a stream of an inert gas and then washed with 300 mL of distilled water. This procedure was repeated until the amount of sulfuric acid remaining in distilled water after washing became negligible to detect by the elemental analysis to yield an amorphous carbon having sulfonate group introduced therein. In the $^{13}C$ nuclear magnetic resonance spectrum of the amorphous carbon having sulfonate residue introduced therein, a chemical shift of a condensed aromatic carbon 6-membered ring was observed near 130 ppm and a chemical shift of a condensed aromatic carbon 6-membered ring having a sulfonate group bonded thereto was observed near 140 ppm. In the powder X-ray diffraction pattern of the sulfonated amorphous carbon, diffraction peaks of carbon (002) face and carbon (004) face were confirmed. The half-value width (2θ) of the diffraction peak of carbon (002) face was 8°. The sulfonate density of the amorphous carbon having sulfonate residue introduced therein was 4.2 mmol/g.

The powdery amorphous carbon having sulfonate residue introduced therein was shaped under pressure under the same conditions as in Example 4 to prepare a disk having a thickness of 0.7 mm and a diameter of 10 mm. Platinum was deposited on one side of the disk and the proton conductivity was then determined in accordance with the alternating current impedance method described above. It was confirmed that the proton conductivity of the sulfonated amorphous carbon was $7\times10^{-2}$ Scm$^{-1}$. This result demonstrates that the amorphous carbon having sulfonate residue introduced therein has a proton conductivity comparable to that of Nafion.

(2) Use of Sulfonated Amorphous Carbon Produced from Toluene as Solid Acid

The sulfonated amorphous carbon powder was evacuated under vacuum at 150° C. for 1 hour. To a mixed solution of 0.1 mol of acetic acid and 1.0 mol of ethyl alcohol was added 0.2 g of the product as a catalyst under an argon atmosphere. The resulting solution was stirred at 70° C. for 6 hours. The rate of production of ethyl acetate during this reaction was determined by gas chromatography. The result was shown as "B (starting material: toluene)" in FIG. 4. As shown in FIG. 7 as "B", the production of ethyl acetate was remarkably rapid in the presence of the amorphous carbon having sulfonate residue introduced therein, demonstrating that this substance functioned as a strong solid acid catalyst.

Example 6

(1) Production of Sulfonated Amorphous Carbon from Glucose

Ten grams of D-glucose was heated at 250° C. for 15 hours in a stream of an inert gas to yield a brown organic powder [a diffraction peak of carbon (002) face whose half-value width (2θ) was 30° was observed]. Five grams of the powder was added to 200 mL of 96% sulfuric acid. The mixture was heated at 150° C. for 15 hours while blowing nitrogen gas into the mixture at a rate of 30 ml/min to yield a black solid. The black solid washed with 300 mL of distilled water. This procedure was repeated until the amount of sulfuric acid remaining in distilled water after washing became negligible to detect by the elemental analysis to yield an amorphous carbon having sulfonate group introduced therein. In the $^{13}$C nuclear magnetic resonance spectrum of the sulfonated amorphous carbon, a chemical shift of a condensed aromatic carbon 6-membered ring was observed near 130 ppm and a chemical shift of a condensed aromatic carbon 6-membered ring having a sulfonate group bonded thereto was observed near 140 ppm. In the powder X-ray diffraction pattern of the sulfonated amorphous carbon, a diffraction peak of carbon (002) face was confirmed. The half-value width (2θ) of the diffraction peak of carbon (002) face was 20°. The sulfonate density of the amorphous carbon having sulfonate residue introduced therein was 4.5 mmol/g.

The powdery amorphous carbon having sulfonate residue introduced therein was shaped under pressure under the same conditions as in Example 4 to prepare a disk having a thickness of 0.7 mm and a diameter of 10 mm. Platinum was deposited on one side of the disk and the proton conductivity was then determined in accordance with the alternating current impedance method described above. It was confirmed that the proton conductivity of the sulfonated amorphous carbon was $5\times10^{-2}$ Scm$^{-1}$. This result demonstrates that the amorphous carbon having sulfonate residue introduced therein has a proton conductivity comparable to that of Nafion.

(2) Use of Sulfonated Amorphous Carbon Produced from Glucose as Solid Acid

The powdery amorphous carbon having sulfonate residue introduced therein was evacuated under vacuum at 150° C. for 1 hour. To a mixed solution of 0.1 mol of acetic acid and 1.0 mol of ethyl alcohol was added 0.2 g of the product as a catalyst under an argon atmosphere. The resulting solution was stirred at 70° C. for 6 hours. The rate of production of ethyl acetate during this reaction was determined by gas chromatography. The result was shown as "C (starting material: glucose)" in FIG. 4. As shown in FIG. 7 as "C", the production of ethyl acetate was remarkably rapid in the presence of the amorphous carbon having sulfonate residue introduced therein, demonstrating that this substance functioned as a strong solid acid catalyst.

Test Example 5

Evaluation of Thermal Stability

The amorphous carbons having sulfonate residue introduced therein produced in Examples 4 to 6 were determined on their decomposition temperatures by temperature-programmed desorption method (Bel Japan, Inc., Japan; Multitask TPD) and thermogravimetric analysis method (Shimadzu Corporation, Japan; DTG-60/60H).

As a result, it was confirmed that the amorphous carbons having sulfonate residue introduced therein of Examples 4, 5 and 6 had decomposition temperatures of 250° C., 220° C. and 200° C., respectively, and that all of these substances had high thermal stability.

Test Example 6

Evaluation of Chemical Stability

Each of the amorphous carbons having sulfonate residue introduced therein produced in Examples 4 to 6 was heated together with distilled water for 72 hours in an autoclave of 150° C. A powder was collected by filtration and evacuated under vacuum at 150° C. for 1 hour. Using 0.2 g of the product as a catalyst, the production reaction for ethyl acetate was performed in the same manner as in Examples 4 to 6. All of these heat-treated sulfonated amorphous carbons exhibited the same catalytic activities as those of the heat-untreated counterparts (not shown). These results demonstrate that the sulfonated amorphous carbons have high chemical stability and that the acid strength is not deteriorated even in hot water of 150° C.

The specification includes all or part of the contents as described in the specification and/or drawings of Japanese Patent Application Nos. 2003-322400 and 2004-84527, which are priority documents of the present application. All publications, patents and patent applications cited herein are incorporated herein by reference in their entirety.

The invention claimed is:

1. A proton conductor material comprising a sulfonated amorphous carbon, wherein
the sulfonated amorphous carbon has a sulfonate density of 1.6 to 8 mmol/g,
in the sulfonated amorphous carbon, chemical shifts of a condensed aromatic carbon 6-membered ring and a condensed aromatic carbon 6-membered ring having a sulfonate group bonded thereto are detected in a $^{13}$C nuclear magnetic resonance spectrum, at least a diffraction peak of carbon (002) face whose half-value width (2θ) is in the range of 5 to 30 is detected in powder X-ray diffractometry, and the sulfonated amorphous carbon exhibits proton conductivity.

2. The proton conductor material according to claim 1, wherein the sulfonated amorphous carbon has a proton conductivity of 0.01 to 0.2 Scm$^{-1}$ as measured by alternating current impedance method under the conditions of a temperature of 80° C. and a humidity of 100%.

3. The proton conductor material according to claim 1 or 2, wherein the sulfonated amorphous carbon has a sulfur content of 0.3 to 15 atm %.

4. The proton conductor material according to claim 1, wherein the sulfonated amorphous carbon is produced by heat treatment of an aromatic hydrocarbon in concentrated sulfuric acid or fuming sulfuric acid.

5. The proton conductor material according to claim 4, wherein the heat treatment is performed at a temperature of 100° C. to 350° C.

6. The proton conductor material according to claim 4 or 5, wherein the aromatic hydrocarbon is at least one substance selected from the group consisting of benzene, naphthalene, anthracene, peryrene and coronene.

7. The proton conductor material according to claim 1, wherein the sulfonated amorphous carbon is produced by heat treatment of a partially carbonized organic compound in concentrated sulfuric acid or fuming sulfuric acid.

8. The proton conductor material according to claim 7, wherein the organic compound is glucose or cellulose.

9. The proton conductor material according to claim 1, wherein only a diffraction peak of carbon (002) face is detected in powder X-ray diffractometry.

10. The proton conductor material according to claim 1, wherein the sulfonated amorphous carbon has a sulfonate density of 3 to 8 mmol/g.

11. A sulfonated amorphous carbon wherein chemical shifts of a condensed aromatic carbon 6-membered ring and a condensed aromatic carbon 6-membered ring having a sulfonate group bonded thereto are detected in a $^{13}$C nuclear magnetic resonance spectrum and that at least a diffraction peak of carbon (002) face whose half-value width (2θ) is in the range of 5 to 30 is detected in powder X-ray diffractometry, the sulfonated amorphous carbon exhibiting proton conductivity and wherein the sulfonated amorphous carbon has a sulfonate density of 1.6 to 8 mmol/g.

12. The sulfonated amorphous carbon according to claim 11, wherein only a diffraction peak of carbon (002) face is detected in powder X-ray diffractometry.

13. The sulfonated amorphous carbon according to claim 11 or 12, the sulfonated amorphous carbon has a sulfonate density of 3 to 8 mmol/g.

14. The sulfonated amorphous carbon according to claim 11, wherein the sulfonated amorphous carbon has a proton conductivity of 0.01 to 0.2 Scm$^{-1}$ as measured by alternating current impedance method under the conditions of a temperature of 80° C. and a humidity of 100%.

15. A process for producing a sulfonated amorphous carbon as recited in claim 11, comprising a step of performing heat treatment of an organic compound in concentrated sulfuric acid or fuming sulfuric acid.

16. The process for producing a sulfonated amorphous carbon according to claim 15, wherein the step of performing heat treatment of an organic compound in concentrated sulfuric acid or fuming sulfuric acid is conducted in a stream of an inert gas or dry air.

17. The process for producing a sulfonated amorphous carbon according to claim 15, further comprising, after the step of performing heat treatment of an organic compound in concentrated sulfuric acid or fuming sulfuric acid, a step of heating the heat-treated product under vacuum evacuation.

* * * * *